(12) United States Patent
Cambridge

(10) Patent No.: US 10,342,731 B2
(45) Date of Patent: Jul. 9, 2019

(54) LUBRICATION DEVICE AND SYSTEM FOR INCREASED PLEASURE

(71) Applicant: THIKA HOLDINGS LLC, St. Pete Beach, FL (US)

(72) Inventor: Vivien Johan Cambridge, Myrtle Beach, SC (US)

(73) Assignee: THIKA HOLDINGS LLC, St. Pete Beach, FL (US)

(*) Notice: Subject to any disclaimer, the term of this patent is extended or adjusted under 35 U.S.C. 154(b) by 26 days.

(21) Appl. No.: 15/220,836

(22) Filed: Jul. 27, 2016

(65) Prior Publication Data

US 2017/0189263 A1 Jul. 6, 2017

Related U.S. Application Data

(60) Provisional application No. 62/274,348, filed on Jan. 3, 2016.

(51) Int. Cl.
| | | |
|---|---|---|
| *A61H 5/00* | (2006.01) | |
| *A61H 19/00* | (2006.01) | |
| *A61M 35/00* | (2006.01) | |

(52) U.S. Cl.
CPC .......... *A61H 19/32* (2013.01); *A61H 19/40* (2013.01); *A61M 35/003* (2013.01); *A61H 2201/0107* (2013.01); *A61H 2201/0207* (2013.01); *A61H 2201/0228* (2013.01); *A61H 2201/105* (2013.01); *A61H 2201/1207* (2013.01); *A61H 2201/50* (2013.01); *A61H 2201/5012* (2013.01); *A61H 2201/5035* (2013.01); *A61H 2201/5038* (2013.01); *A61H 2201/5061* (2013.01); *A61H 2201/5071* (2013.01); *A61H 2201/5082* (2013.01); *A61H 2201/5097* (2013.01); *A61M 2205/3334* (2013.01); *A61M 2205/3337* (2013.01); *A61M 2205/3368* (2013.01); *A61M 2205/8206* (2013.01); *A61M 2210/167* (2013.01)

(58) Field of Classification Search
CPC ........ A61H 19/00; A61H 19/30; A61H 19/40; A61H 19/44; A61H 19/50; A61M 35/003
USPC ......................................... 600/38–41; 601/46
See application file for complete search history.

(56) References Cited

U.S. PATENT DOCUMENTS

| | | |
|---|---|---|
| 5,782,818 A | 7/1998 | Shubin |
| 5,807,360 A | 9/1998 | Shubin |
| 6,749,557 B2 | 6/2004 | Garland |
| 7,163,508 B1 | 1/2007 | Washington |
| 9,050,240 B2 | 9/2015 | Howsam |
| 2009/0171144 A1 | 7/2009 | Squicciarini |
| 2009/0275796 A1 | 11/2009 | Gil |
| 2011/0000493 A1 | 1/2011 | Amer |
| 2013/0060081 A1 | 3/2013 | Carter et al. |

(Continued)

OTHER PUBLICATIONS

International Search Report and Written Opinion dated Oct. 6, 2016 received in the corresponding PCT Application (PCT/US16/044207).

*Primary Examiner* — John P Lacyk
(74) *Attorney, Agent, or Firm* — Volpe and Koenig, P.C.

(57) ABSTRACT

A masturbation assembly is disclosed in the present application that provides an improved lubrication mechanism that allows a user to apply and reapply lubricant with minimal time and effort. In one embodiment, the masturbation assembly includes a heating element to heat the lubricant. In another embodiment, the masturbation assembly is motorized.

18 Claims, 17 Drawing Sheets

(56) References Cited

U.S. PATENT DOCUMENTS

| | | |
|---|---|---|
| 2013/0324792 A1 | 12/2013 | Mizrahi et al. |
| 2014/0107409 A1* | 4/2014 | Bailey .................. E03D 9/08 600/38 |
| 2015/0164736 A1* | 6/2015 | Gallant ................ A61M 31/00 600/38 |
| 2015/0366748 A1 | 12/2015 | Cambridge |

* cited by examiner

US 10,342,731 B2

LUBRICATION DEVICE AND SYSTEM FOR INCREASED PLEASURE

CROSS REFERENCE TO RELATED APPLICATIONS

This application claims the benefit of U.S. provisional patent application 62/274,348, filed on Jan. 3, 2016, which is incorporated by reference as if fully set forth.

FIELD OF INVENTION

The present application is generally related to a masturbation device and is more particularly related to lubrication device and system for increased pleasure, and a device and system for providing lubrication to masturbation devices of all kinds of masturbation devices.

BACKGROUND

Several known masturbation devices presently exist that are used by both men and women.

For men, existing masturbation devices are generally manual devices that include a hard outer housing and a soft interior sleeve. The sleeve is generally molded to resemble a human orifice and is dimensioned to accommodate a sex organ. The device typically includes a removable cap to access the interior of the sleeve and outer housing. The cap generally includes threading to allow quick attachment and detachment to the assembly. The outer housing also typically includes an opening used for exhaust, i.e. air, and for cleaning. A user manually maneuvers the device back and forth to cause a sensation on the user's sex organ. Some known masturbation devices are disclosed in U.S. Pat. Nos. 5,782,818 and 5,807,360.

Lubricant may be manually applied to the interior of the sleeve to reduce friction between the sex organ and the sleeve and increase a user's pleasure. During usage, lubricant is dissipated or absorbed and the effectiveness of the lubricant diminishes. The user must then stop stimulation, manually remove the cap from the device, and supply more lubricant. Other known masturbation devices include life sized or "real" dolls that resemble humans. Such dolls have orifices for insertion. A user must manually apply lubricant to such devices.

Female masturbation devices include stimulators, dildos, vibrators and insertion devices of various kinds. Such devices must be manually coated with a lubricant if that is desired by a user.

It would be desirable to have a masturbation supply device that allows for automatic application of lubrication that is also easy to use.

It would further be desirable to have a masturbation device that allows for application of lubrication in a focused area where pleasure is desired.

It would further be desirable to have a masturbation device that provides lubrication at a selected or desired time.

SUMMARY

A masturbation assembly is disclosed in the present application that provides an improved lubrication mechanism providing for the application of lubricant with minimal effort. In one embodiment, the masturbation assembly includes a heating element to heat the lubricant. In another embodiment, the masturbation assembly is motorized.

In an aspect of the present invention, a masturbation assembly is provided including a housing, a reservoir in communication with the housing where the reservoir is configured to retain a quantity of lubricant, and a valve controlling the passage of the lubricant from the reservoir to the housing. The valve can be actuated by a user, or automatically actuated. Various types of valves can be used according to the invention.

DETAILED DESCRIPTION OF THE PREFERRED EMBODIMENTS

Figure 1:
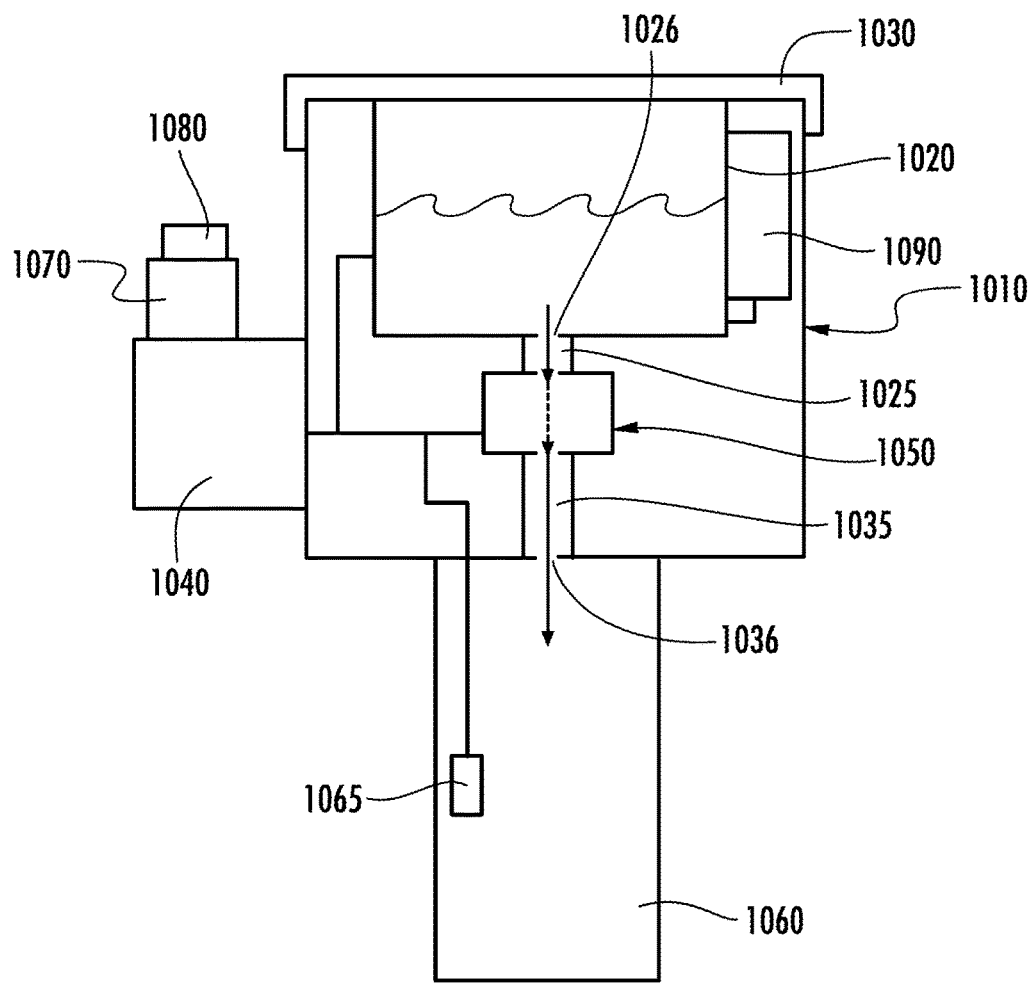
FIG. 1 is a cross-sectional view of a lubricant supply assembly.

FIG. 1 illustrates a lubricant supply assembly including a housing 1010 that defines a lubricant reservoir 1020. The term "lubricant" is used herein to describe the fluid held in the lubricant reservoir 1020 that is used for lubrication of body parts during masturbation or sex, and encompasses oils, water based gels, silicon based gels, K-Y JELLY™, ASTROGLIDE™, and other lubricants known in the art. Moreover, one of ordinary skill in the art will recognize that other fluids could be contained within the lubricant reservoir 1020.

A cap 1030 is provided on an end of the housing 1010. The cap 1030 preferably is screwed onto a correspondingly threaded portion of the housing 1010. An actuator assembly 1040 is provided in communication with the housing 1010. Specifically, the actuator assembly 1040 is in communication with a valve assembly 1050 within the housing 1010. A simplified line of communication is shown in FIG. 1 between the actuator assembly 1040 and the valve assembly 1050, which can include any form of communication capable of sending signals from the actuator assembly 1040 to the valve assembly 1050. The valve assembly 1050 preferably includes a one-way check valve that controls the flow and volume of lubricant exiting the lubricant reservoir 1020. The actuator assembly 1040 can include a pump that controls and/or drives the flow of lubricant through the valve body 1050.

A first conduit 1025 is defined between the lubricant reservoir 1020 and the valve body 1050, and a second conduit 1035 is defined between the valve body 1050 and a delivery assembly 1060. A first port 1026 is provided at an end of the first conduit 1025 in communication with the lubricant reservoir 1020, and a second port 1036 is provided at an end of the second conduit 1035 in communication with the delivery assembly 1060. The first conduit 1025 and the second conduit 1035 provide a channel to deliver lubricant from the lubricant reservoir 1020 to the delivery assembly 1060. One of ordinary skill in the art recognizes that the first conduit 1025 and second conduit 1035 can include check valves to prevent the backflow of lubricant. Other hydraulic fluid regulators can be provided in the first conduit 1025 and/or the second conduit 1035 to provide for reliable flow of lubricant from the lubricant reservoir 1020 to the delivery assembly 1060. Generally, the assembly of FIG. 1 provides an improved configuration for delivering lubricant from the lubricant reservoir 1020 to the delivery assembly 1060, i.e. the lubricant receiving portion.

The delivery assembly 1060 is shown generically in FIG. 1, but can include any shape, for example a sleeve configured to receive a male sex organ or a phallic shaped object. Further embodiments of types and shapes of delivery assemblies are described below with respect to the other figures.

The delivery assembly 1060 of FIG. 1 preferably includes a sensor 1065. The sensor 1065 can include any known type of sensor, including a piezoelectric sensor, shock sensor, motion sensor, pressure sensor, temperature sensor, break-beam sensor, etc. The sensor 1065 is configured to detect any type of stimulus inside or adjacent to the delivery assembly 1060 and generate a signal related to the stimulus. The signal can then be used to vary the amount, temperature, frequency, or any other variable related to the lubricant being delivered to the delivery assembly 1060.

The actuator assembly 1040 preferably includes a CPU unit 1070 with a memory unit, power supply, and processor. The power supply can include any known power supply configuration, such as a battery. A transmitter/receiver unit 1080 is also provided in communication with the CPU unit 1070. The transmitter/receiver unit 1080 can be in wired or wireless communication with an external signaling source, such as the internet, via Bluetooth® or Wi-Fi®. The CPU unit 1070 can store pre-programmed signal impulses regarding frequency, volume, temperature, and other lubricant variables. The CPU unit 1070 can also be in communication with a videogame application that sends impulses to the CPU unit 1070 based on events in the videogame application. Based on these received impulses or signals, different variables regarding the delivery of lubricant to the delivery assembly 1060 are adjusted.

A heater unit 1090 is provided adjacent to the lubricant reservoir 1020 in the housing 1010. The heater unit 1090 is provided to heat lubricant in the lubricant reservoir 1020 prior to delivery to the delivery assembly 1060. The heater unit 1090 can receive signals from the CPU unit 1070 regarding variables for heating the lubricant, such as duration, temperature, etc. Simplified communication lines are illustrated between the actuator assembly 1040, the sensor 1065 of the delivery assembly 1060, the lubricant reservoir 1020, and the heater unit 1090, however one of ordinary skill in the art would recognize that any form of communication, both electrical and hydraulic, could be provided between these components.

Figure 2A:
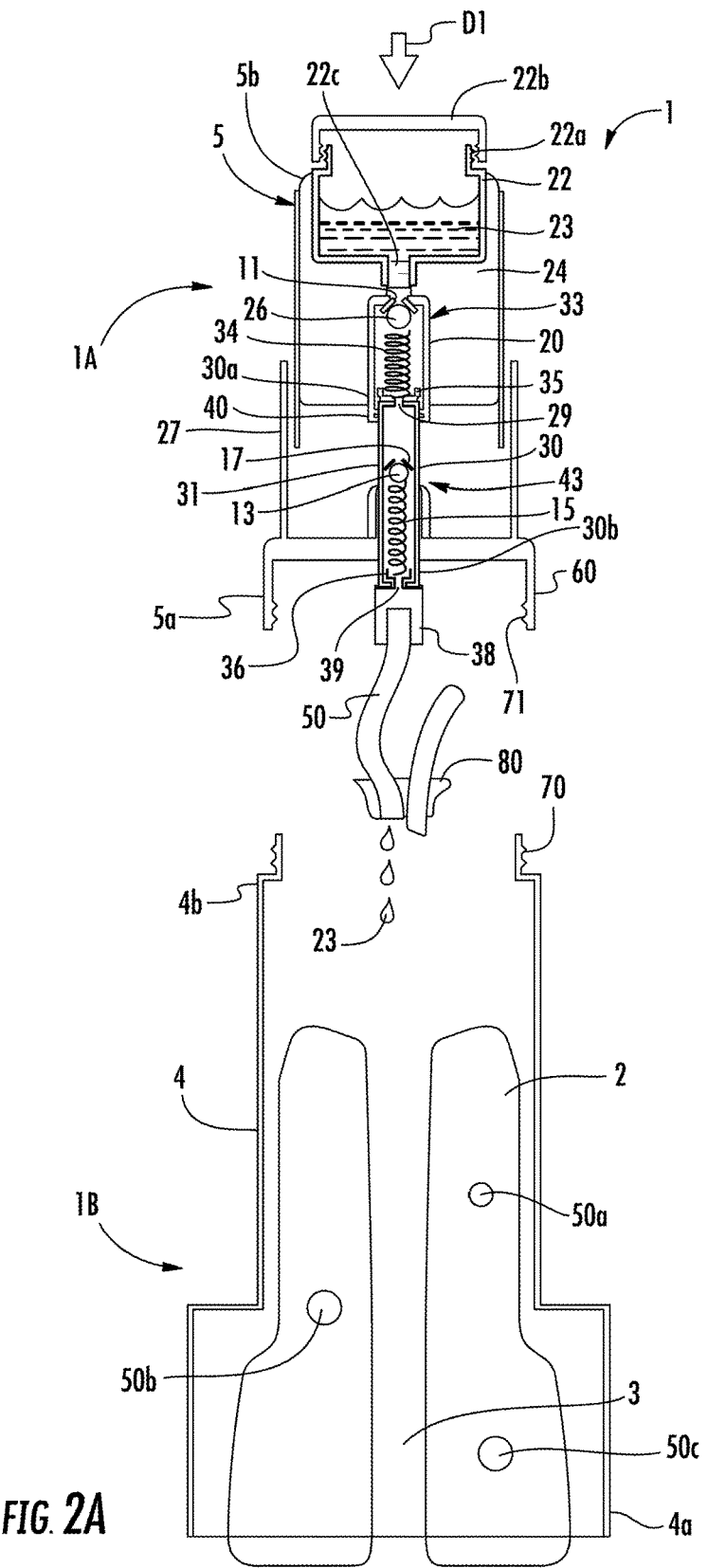
FIGS. 2A-2C are cross-sectional views of a masturbation assembly according to a first embodiment.
Figure 2B:
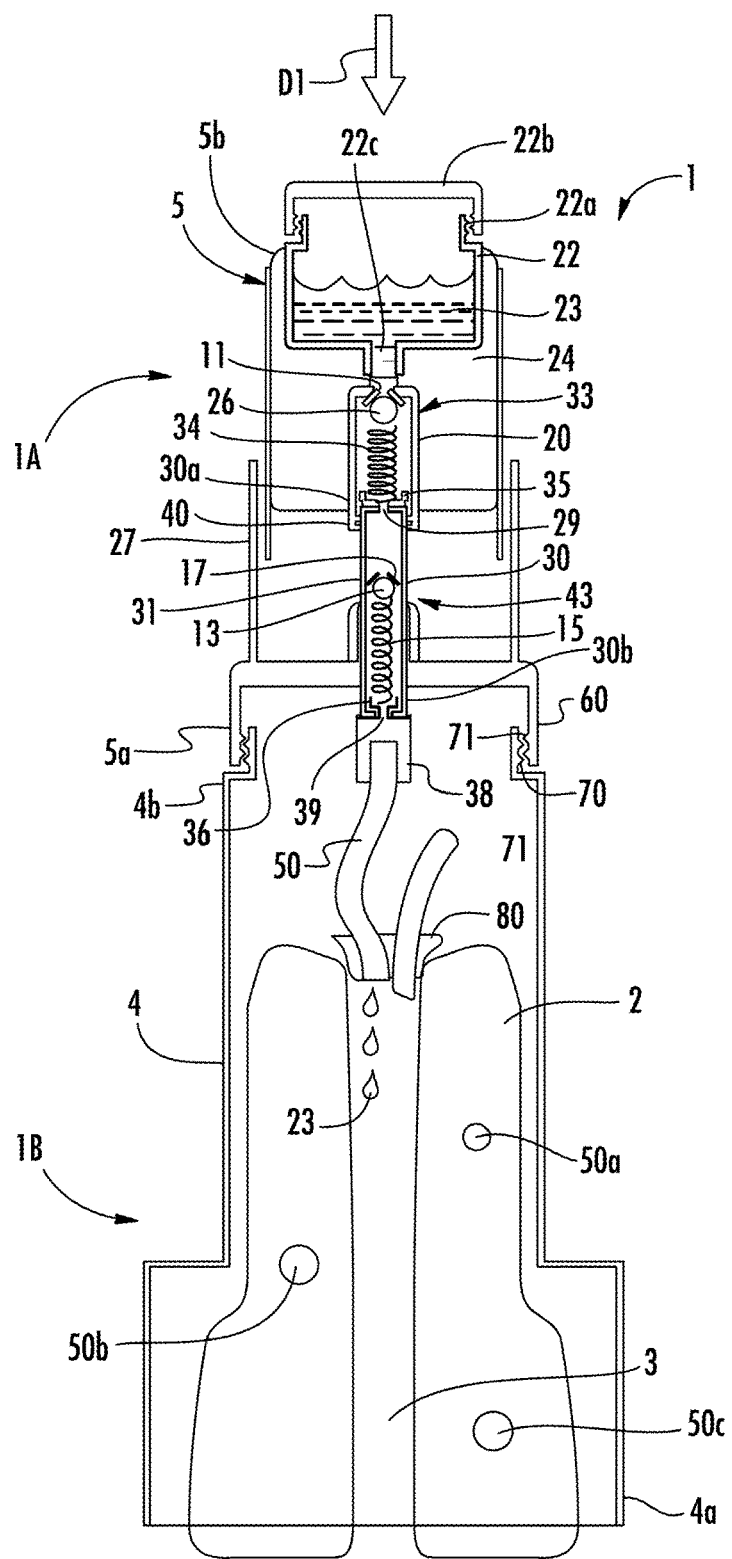
Figure 2C:
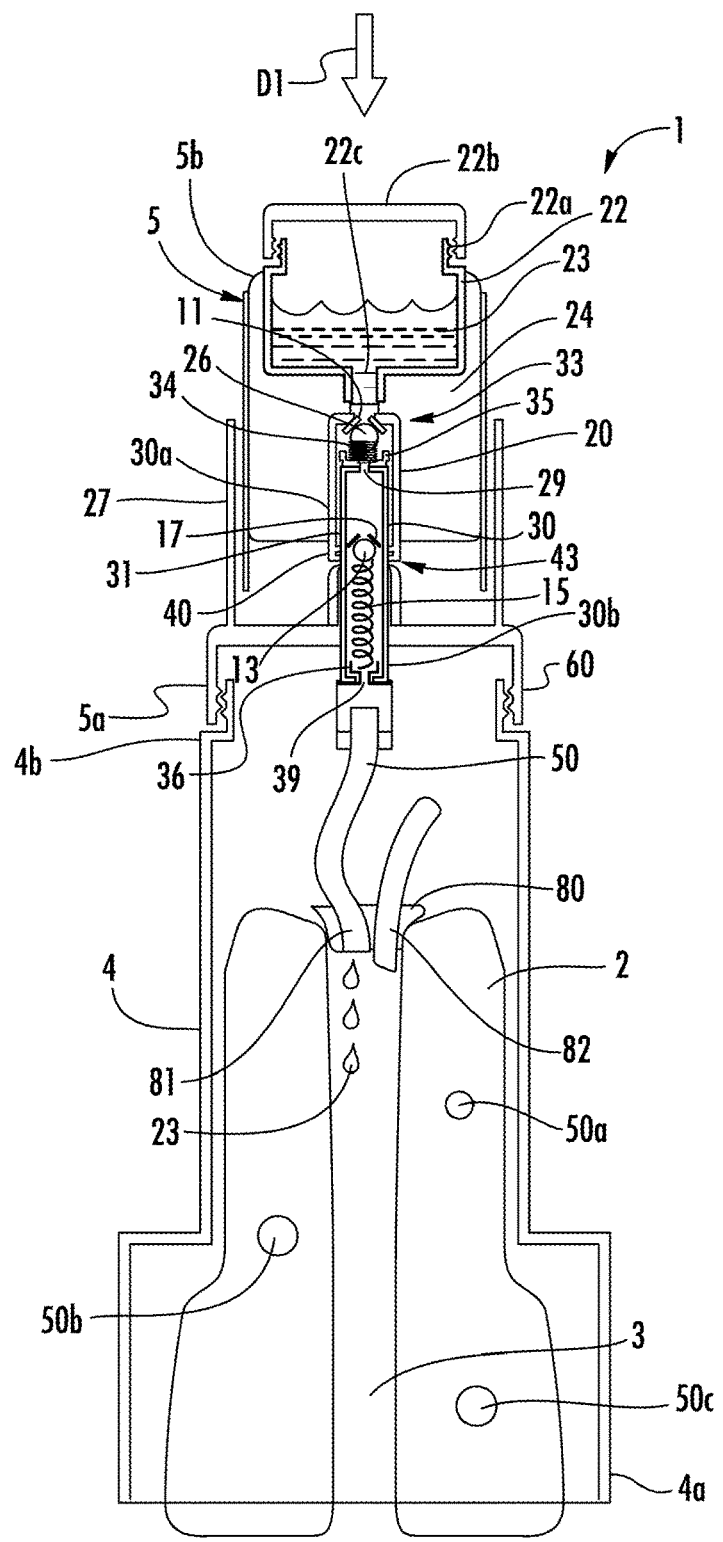

Referring now to FIGS. 2A-2C, 3, and 4, a masturbation assembly 1 according to an embodiment includes a first housing 4 and a second housing 5, with the first housing 4 shown in the bottom half of FIGS. 2A-2C and the second housing 5 shown in the top half of FIGS. 2A-2C. The embodiment of FIGS. 2A-2C, 3, and 4 can be considered a manual masturbation assembly, in that the dispensing of lubricant is initiated, actuated, and/or controlled by the pressing action of a user. The first housing 4 includes an orifice 3 at a first end 4a opposite from the second housing 5. The first housing 4 is fixed to a first end 5a of the second housing 5 at a second end 4b of the first housing 4. The first end 5a includes a transition portion 60 that connects the first housing 4 and the second housing 5.

A soft, plastic material sleeve 2 is arranged within the first housing 4 and is in communication with the orifice 3. The sleeve 2 is preferably formed from a polymeric gel. The sleeve 2 is semi-rigid and elastically deformable to accommodate a user's sex organ, i.e. a penis. As shown in FIGS. 2A-2C and 3, the sleeve 2 extends axially beyond the first housing 4. This configuration ensures that during usage, contact is limited between the user's sex organ to only the sleeve 2 of the assembly 1, and not the hard outer first housing 4. A length of the sleeve 2 is preferably more than half of a length of the first housing 4. This arrangement provides for a compact axial footprint of the overall assembly 1.

In one embodiment, the first housing 4 is similar to the masturbation shell, shown as element 101 in U.S. Provisional App. 62/191,063, which is incorporated by reference herein as if fully set forth. The first housing 4 can include sensation imparting elements, such as bumps, protrusions or beads along an interior of the first housing 4 within the sleeve 2 for providing increased sensation as described in U.S. Provisional App. 62/191,063.

As shown in FIGS. 2A-2C, the second housing 5 includes a containment vessel 22 that forms a reservoir on an axially opposite end 5b of the second housing 5 from the first housing 4. The containment vessel 22 includes a reservoir of lubricant 23, and is in fluid connection with a first hollow cylindrical member 20 via a port 22c.

As shown in FIGS. 2A-2C, in one embodiment, a top portion 1A of the assembly 1 is a lubricant supply assembly 1A, and the bottom portion 1B is a sex toy housing 1B. The lubricant supply assembly 1A includes the lubricant reservoir 23 and a lubricant delivery assembly axially below the lubricant reservoir 23. The lubricant delivery assembly is defined by a dispensing spout 50 and the elements axially between the reservoir 23 and the dispensing spout 50. The top portion 1A includes a threading 71 that is configured to engage with a corresponding threading 70 at a terminal engagement end on the bottom portion 1B, as shown in FIGS. 2A-2C. Using these threadings 70, 71, the lubricant supply assembly 1A can be matingly engaged with and secured to an existing sex toy housing 1B. A user can twist the top portion 1A with respect to the bottom portion 1B to secure the two portions to each other. One of ordinary skill in the art would recognize that other securing means can be used, such as a stretchable gripping ring on an end of the top portion 1A that engages with an end of the bottom portion 1B. In one embodiment, a lubricant delivery assembly is defined by the conduits extending between the lubricant reservoir downward to a dispensing spout 50 and plug 80, which engages in the bottom portion 1B.

The containment vessel 22 includes a screw thread 22a which matingly engages with a corresponding threaded cap 22b for closing the containment vessel 22. Once the containment vessel 22 is matingly attached to the threaded cab 22b, the lubricant 23 is captively secured within the containment vessel 22 and cannot leak or otherwise spill out of the assembly 1. One of ordinary skill in the art would recognize from the present application that other configurations could be used to seal the lubricant 23 within the containment vessel 22.

The first hollow cylindrical member 20 houses a valving system for controlling and/or regulating the supply of lubricant from the containment vessel 22 to the interior of a portion of the first housing 4. A first check valve 33 preferably comprises a first valve seat 11 arranged adjacent to the containment vessel 22 at an end of the port 22c, a first valve ball 26 or stopper, and a first spring 34 for pressing the first valve ball 26 against the first valve seat 11 to block the port 22c. The first valve seat 11, the first valve ball 26, and the first spring 34 form the first check valve 33 within the first hollow cylindrical member 20 to prevent lubricant 23 from inadvertently leaking out of the containment vessel 22 via the port 22c. One of ordinary skill in the art would recognize from the present application that other variations of a check valve could be used within the first hollow cylindrical member 20 to control and/or regulate the supply or passage of lubricant. Other known check valves include a diaphragm check valve, a swing check valve, or a lift check valve.

The first hollow cylindrical member 20 connects to a first cap 35 including a first through-hole 29. The first through-hole 29 provides a fluid communication path from the first hollow cylindrical member 20 to a second hollow cylindrical member 30. A first axial end 30a of the second hollow cylindrical member 30 is connected to the first hollow cylindrical member 20, and a second axial end 30b of the second hollow cylindrical member 30 terminates at a dispensing spout 50. The second hollow cylindrical member 30 includes an outer wall 31 that defines an inner chamber.

As shown in FIGS. 2A-2C, the containment vessel 22 and the first hollow cylindrical member 20 are arranged concentrically within a dispensing button 24, which is preferably cylindrical. The dispensing button 24 is concentrically arranged within an outer shell 27 of the second housing 5. Although not explicitly illustrated, the dispensing button 24 can be slidably and captively sealed within the outer shell 27. The dispensing button 24 is configured to actuate one or more valves within the assembly 1 to allow a user to dispense lubricant from the containment vessel 22 through the dispensing spout 50 to the sleeve 2 by applying an axially downward pressure on the dispensing button 24.

A second check valve 43 may also be included as part of the valving system. The second hollow cylindrical member 30 is similar to the first hollow cylindrical member 20 and includes the second check valve 43 with a second valve seat 17, a second valve ball 13, and a second spring 15 for biasing the second valve ball 13 against the second valve seat 17. The second valve 43 effectively creates a vacuum to suck lubricant out of the reservoir and into the first hollow cylindrical member 20.

The second hollow cylindrical member 30 includes a second cap 36 and a piston member 38 on an axially opposite end from the first hollow cylindrical member 20. The second hollow cylindrical member 30 and the piston member 38 effectively form a piston during movement into the first hollow cylindrical member 20. The second cap 36 and the piston member 38 provide a fluid connection to the dispensing spout 50 such that lubricant can flow from the containment vessel 22 to the dispensing spout 50. An outer diameter of the second cap 36 is slightly smaller than an inner diameter of the second hollow cylindrical member 30. The second cap 36 includes a second through-hole 39 that provides a communication pathway to the piston 38 and the dispensing spout 50. The second hollow cylindrical member 30 is concentrically received within the first hollow cylindrical member 20, i.e. an outer diameter of the second hollow cylindrical member 30 is less than an inner diameter of the first hollow cylindrical member 20. The second hollow cylindrical member 30 is slidably received within an enlarged end 40 first hollow cylindrical member 20.

The dispensing spout 50 is preferably a flexible tube defining an inner bore that directs lubricant from the piston 38 to the sleeve 2. A delivery hose 70 is provided that allows air to escape from orifice 3 in the sleeve 2 during use of the assembly 1. The delivery hose 70 is connected at one end to the sleeve 2 via a plug 80. An opposite end of the delivery hose 70 preferably terminates outside of the first housing 4. The plug 80 is inserted into a rear opening of the sleeve 2 opposite from the orifice 3 end of the sleeve 2. The plug 80 preferably includes two ports: a first port 81 dimensioned for receiving an end of the dispensing spout 50 and a second port 82 dimensioned for receiving an end of the delivery hose 70. The plug 80 is preferably semi-malleable such that the plug 80 can be press-fit into an end of the sleeve 2 and remain fixed during operation of the assembly 1. An adhesive or other fastening arrangement can be used to fix the plug 80 to the sleeve 2.

As shown in FIGS. 2A-2C, multiple dispensing spouts 50 can be provided. In one embodiment, the dispensing spouts branch off from a common dispensing spout 50, as shown in FIGS. 2A-2C. The ports for dispensing spouts are shown on the sleeve 2 as ports 50a, 50b, and 50c. This configuration ensures that lubricant 23 is distributed along an entire extent of the sleeve 2 and provides enhanced lubrication to the user's sex organ during usage. The ports 50a, 50b, 50c are spaced axially along the sleeve 2 at an approximately uniform distance from each other. The ports 50a, 50b, 50c are also circumferentially spaced along the interior of the sleeve 2 to provide for more uniform distribution of lubricant 23 than having a single dispensing spout 50 only at an axial end of the sleeve 2.

As shown in FIG. 2C, during operation, user presses down in the axially downward direction (D1) on the containment vessel 22 and causes pressure to build in the first cylindrical member 20 forcing the second ball 13 to disengage from valve seat 17 causing lubricant to flow through dispensing spout 50 into the sleeve 2. After the containment vessel 22 and the first cylindrical member 20 reach their lowest positions, the first spring 34 provides a biasing force that forces the first cylindrical member 20 to move to an initial position. The second ball 13 is biased to once again engage the second valve seat 17 and forms a vacuum in the first cylindrical member 20. The first ball 26 is then forced away from the first valve seat 11 and lubricant 23 is extracted from the containment vessel 22 and into the first cylindrical member 20. Next, if the containment vessel 22 and the first cylindrical member 20 are pressed downward again, then lubricant in the first cylindrical member 20 is discharged from dispensing spout 50.

Figure 2D:
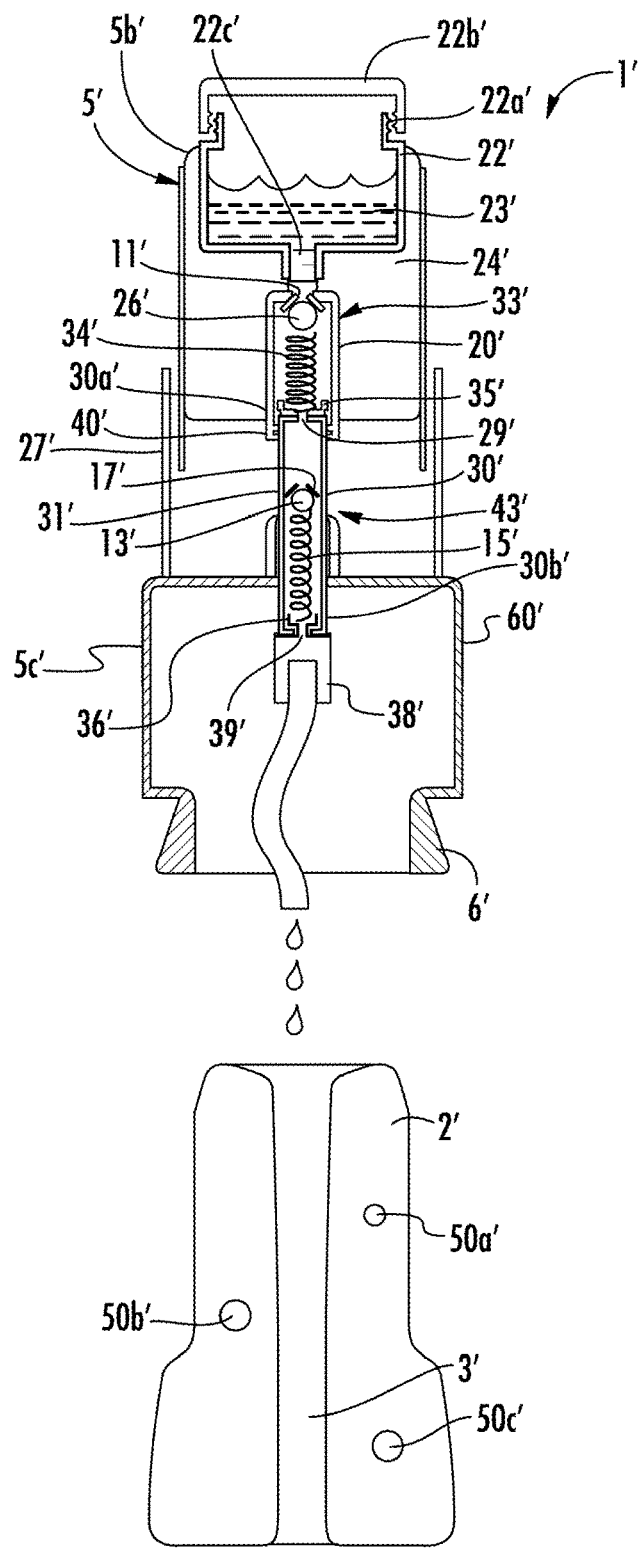
FIGS. 2D and 2E are cross-sectional views of a masturbation assembly according to the first embodiment with an alternative mating interface between a lubricant assembly and a sex toy.
Figure 2E:
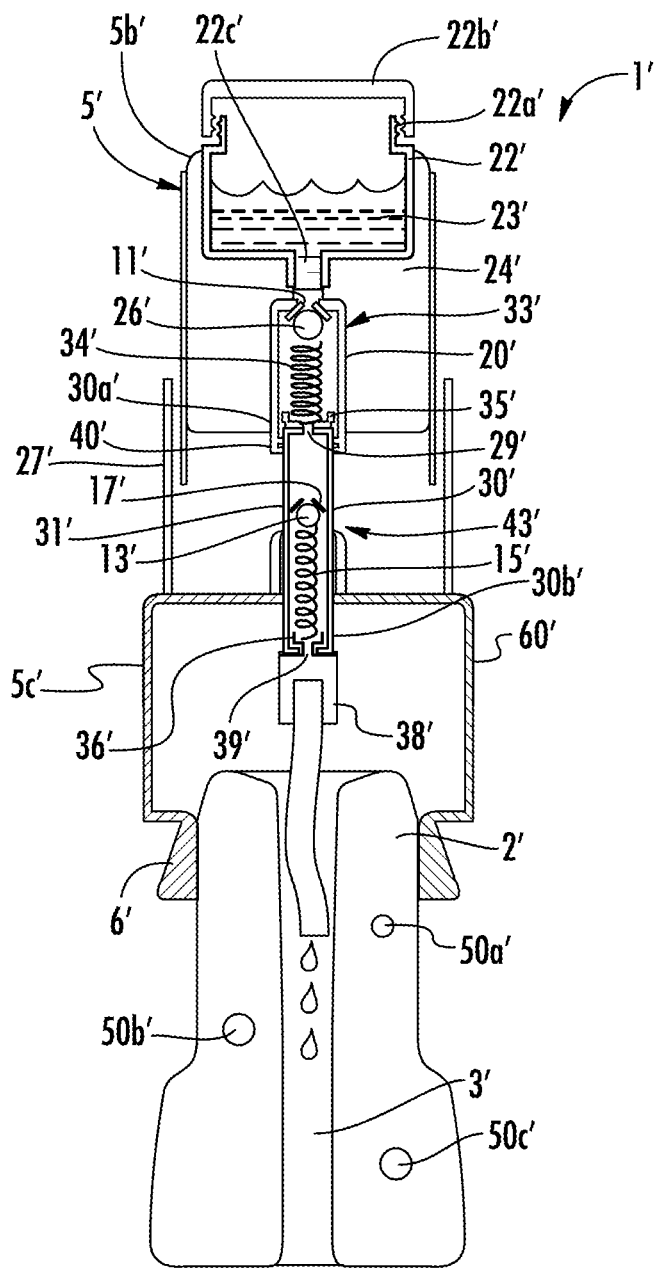
Figure 3:
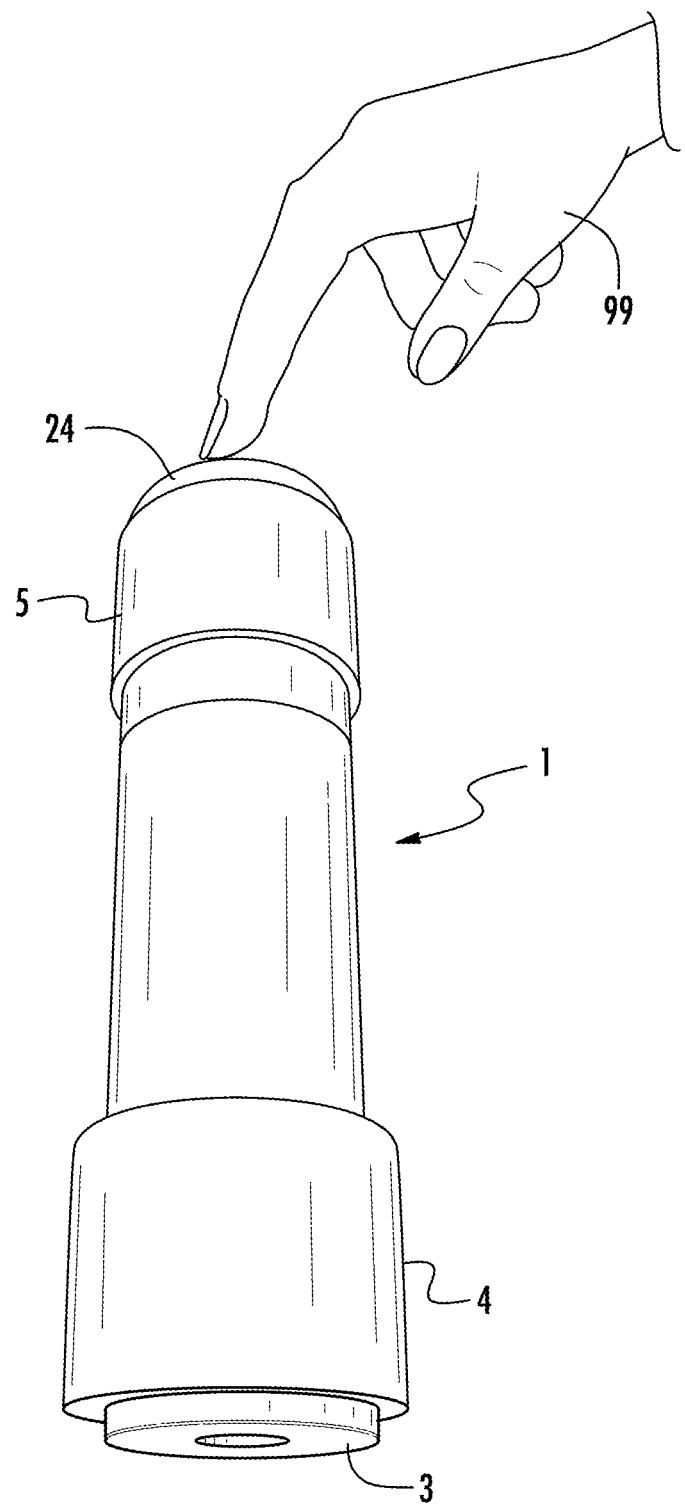
FIG. 3 is a perspective view of the masturbation device of FIGS. 2A-2C as being used by a user.

FIGS. 2D and 2E illustrate an embodiment of a masturbation assembly 1' similar to the first embodiment described above with respect to FIGS. 2A-2C. All of the elements are similar to the elements discussed above with respect to FIGS. 2A-2C and are annotated with a prime notation. Unless specifically discussed with respect to FIGS. 2D and 2E, elements having the same numerical indicator have a substantially similar structure and function as discussed above. In the masturbation assembly 1' of FIGS. 2D and 2E, the masturbation assembly 2' is a self-contained body, i.e. lacks a housing 4 as discussed above. The masturbation assembly 1' includes a housing 5c' connected at one end to the lubrication assembly components, and connected at an opposite end to a sex toy housing 2'. The housing 5c' is preferably a flexible rubber cup-like component with an open end 6'. The open end 6' is dimensioned to accommodate an end of the sex toy 2' opposite from an orifice 3' of the sex toy 2'. The housing 5c' is flexible and the open end 6' of the housing 5c' stretches to wrap around and engage an upper end of the sex toy 2' such that the housing 5c' is fixedly attached to the sex toy 2'. The lubrication assembly above the housing 5c' can then supply lubricant to the sex toy 2' as described herein.

Figure 4:
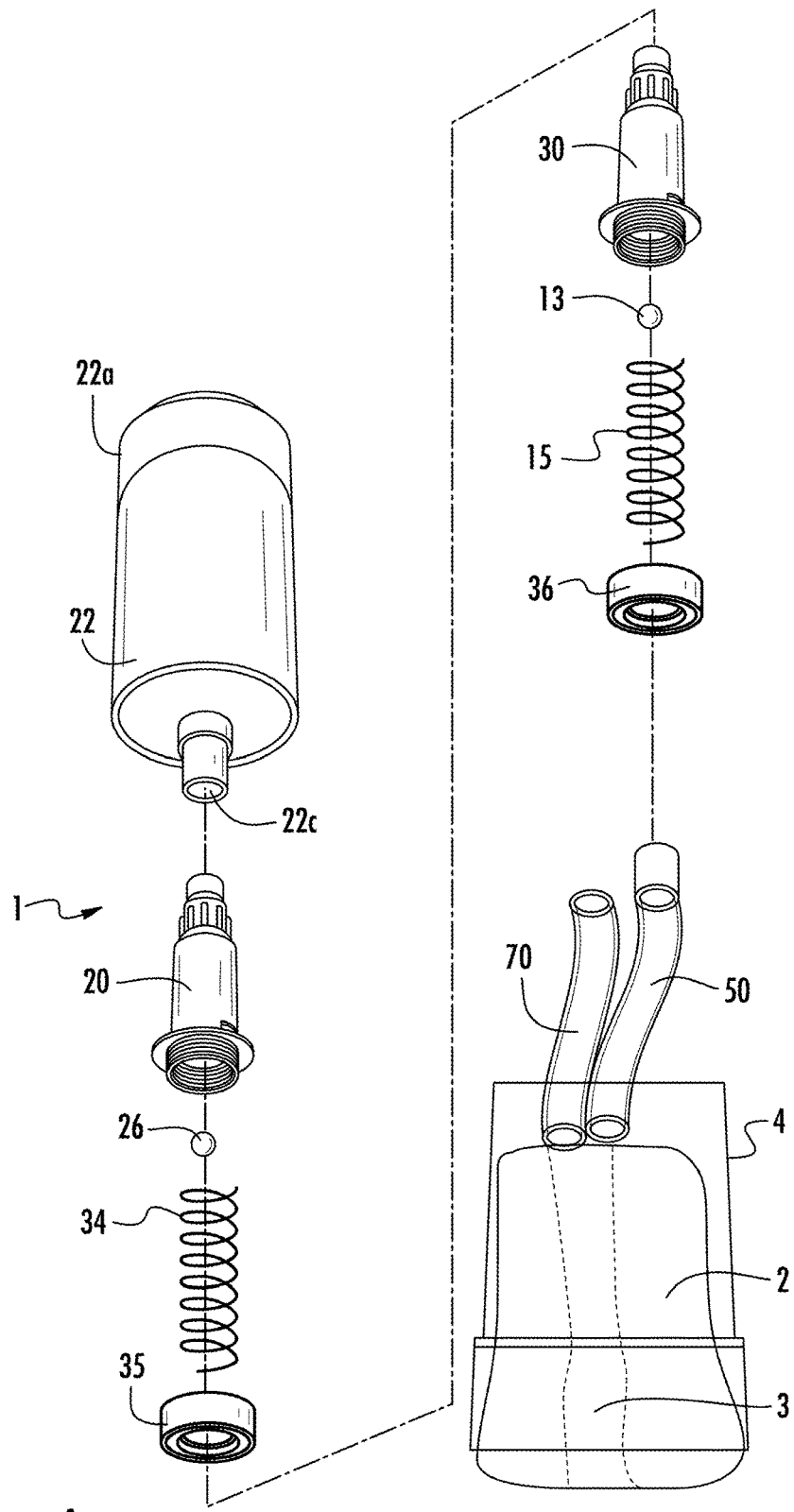
FIG. 4 illustrates a partial, exploded view of the masturbation device of FIGS. 2 and 3.

As shown in FIG. 4, the first cylindrical member 20 and the second cylindrical member 30 include threaded end portions that engage with a respective one of the caps 35, 36.

Figure 5:
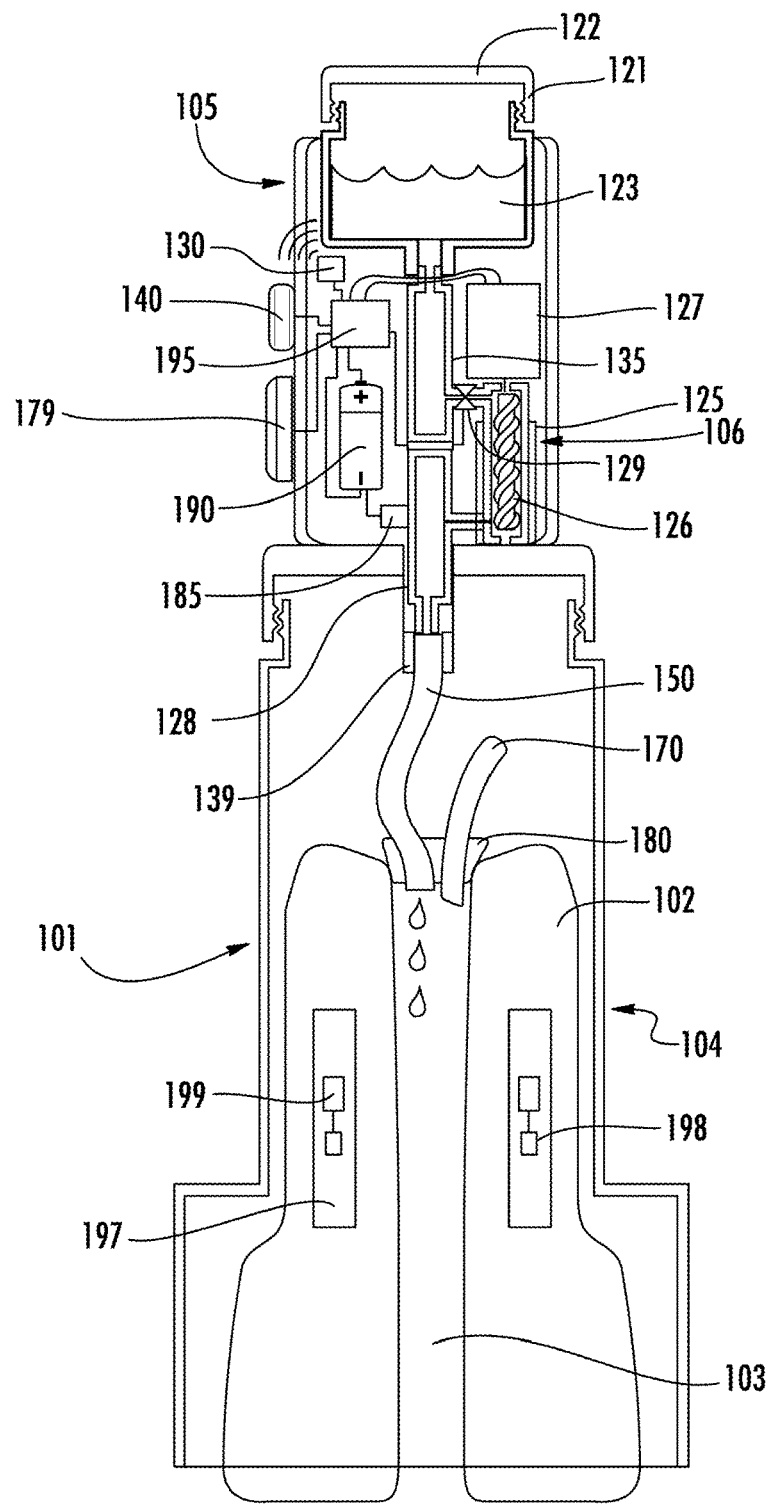
FIG. 5 is a cross-sectional view of a masturbation assembly according to a second embodiment.

A second embodiment of the assembly 101 is shown in FIG. 5. The embodiment of FIG. 5 can be considered a motorized, electric or electrically assisted masturbation assembly, in that the dispensing of lubricant is initiated, actuated, and/or controlled by the pressing action of a user and a motor, such as a battery operated motor. The masturbation assembly preferably includes a first housing 104, an orifice 103, a sleeve 102, and a second housing 105. The assembly 101 of the second embodiment includes a mechanized arrangement 106 for pumping lubricant 123 from the containment vessel 122. As shown in FIG. 5, this assembly 101 includes a positive displacement pumping mechanism which includes an intake vessel 135 in communication with the containment vessel 122 and a displacement vessel 125. As shown in FIG. 5, a valve 129 is arranged between the displacement vessel 125 and the intake vessel 135. The displacement vessel 125 is preferably a cylindrical vessel in which a displacement screw 126 is arranged. The displacement screw 126 is rotationally driven by a motor 127, and rotation of the displacement screw 126 forces lubricant 123 from the containment vessel 122 to the intake vessel 135, through the displacement vessel 125, and into an exhaust vessel 128. Although FIG. 5 illustrates the assembly 101 as including the exhaust vessel 128, one of ordinary skill in the art recognizes that the lubricant 123 could be driven directly from the intake vessel 135 to the displacement vessel 125 and then to the dispensing spout 150. A plug 139 is shown in FIG. 5 as securing an end of the dispensing spout 150 to the exhaust vessel 128.

It is appreciated that the embodiment of FIG. 5 may include any type of pump, such as a push-button battery-operated pump, to control the flow of lubricant from a lubricant reservoir portion to a lubricant delivery portion. Other known types of pumps that can be used include direct lift, displacement, gravity, rotary displacement, reciprocating positive displacement, screw, plunger, impulse, as well as any other known pump to one of ordinary skill in the art.

The assembly 101 of the second embodiment may preferably include a processor 195 which serves to control the operational state of the motor 127. The processor 195 is configured to receive user input and receive wireless data. In an embodiment, the processor 195 includes a Wi-Fi® internet connection or wired internet connection, such that the assembly 101 is configured to receive input from an external source or third party, i.e. not the user. The processor 195 is preferably connected to a wireless transmitter/receiver unit 130. For example, a third party can offer a sexual simulation program that simulates sex with a user via remotely controlling the motor 127 of the assembly 101.

As shown in FIG. 5, the sleeve 102 includes a deformable sleeve 197 with a processor 198 and a motor 199 that manipulates a shape of the deformable sleeve 197 based on input received by the processor 198. The input received by the processor 198 can be sent via the wireless transmitter unit 130 or otherwise delivered to the processor 198. For example, a user can preset a manipulation program for the deformable sleeve 197 which is then maneuvered according to the program, thereby providing additional stimulation to a user's sex organ through the sleeve 102. In one embodiment, a third party remotely controls manipulation of the deformable sleeve 197 and sleeve 102 via a wireless or wired connection through the processor 198.

A dial 140 allows for incremental adjustment of a speed of the motor 127, which also regulates the volume of lubricant 123 that is ultimately delivered to the sleeve 102. Adjusting the dial 140 and the speed of the motor 127 controls the volume of lubricant 123 that is displaced when the motor 127 is activated. A battery 190 provides power to the motor 127 through the processor 195, which can include a controller. The battery 190 is preferably rechargeable and can be charged via an AC/DC power charging cord, a USB charging cord, or other charging arrangement.

The assembly 101 can also include a button 179 for activating a pump 185 to pump lubricant 123 into the sleeve 102. In one embodiment, the button 179 is configured to control the pump 185 such that the pump 185 pumps lubricant 123 directly from the containment vessel 122 to the dispensing spout 150 without requiring operation of the displacement screw 126. The assembly 101 allows a user to press and hold a button 179 and thereby pump lubricant 123 from the containment vessel 122 into the sleeve 102. When a user releases the button 179, the pumping action ceases.

Figure 6A:
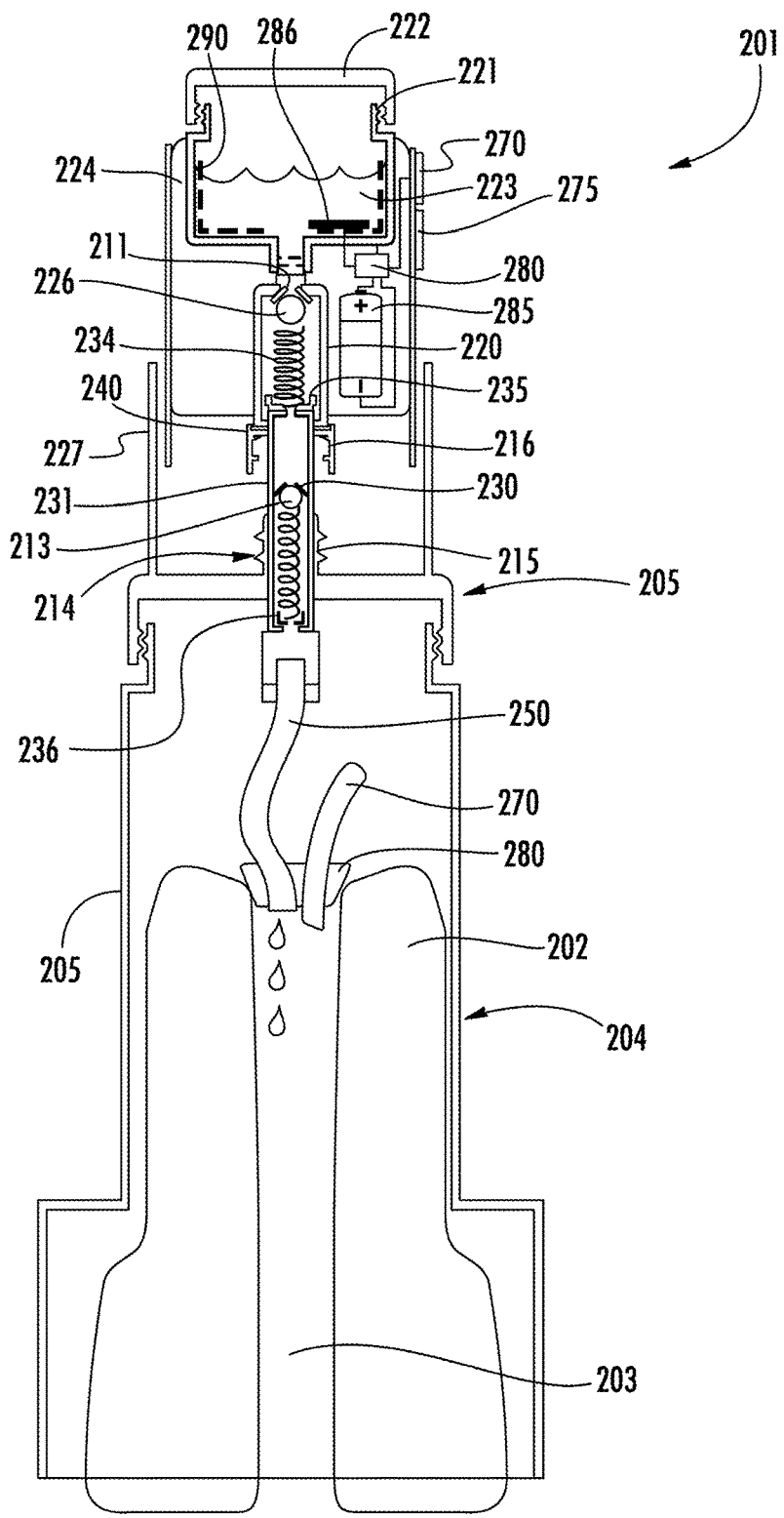
FIGS. 6A and 6B are cross-sectional views of a masturbation assembly according to a third embodiment.
Figure 6B:
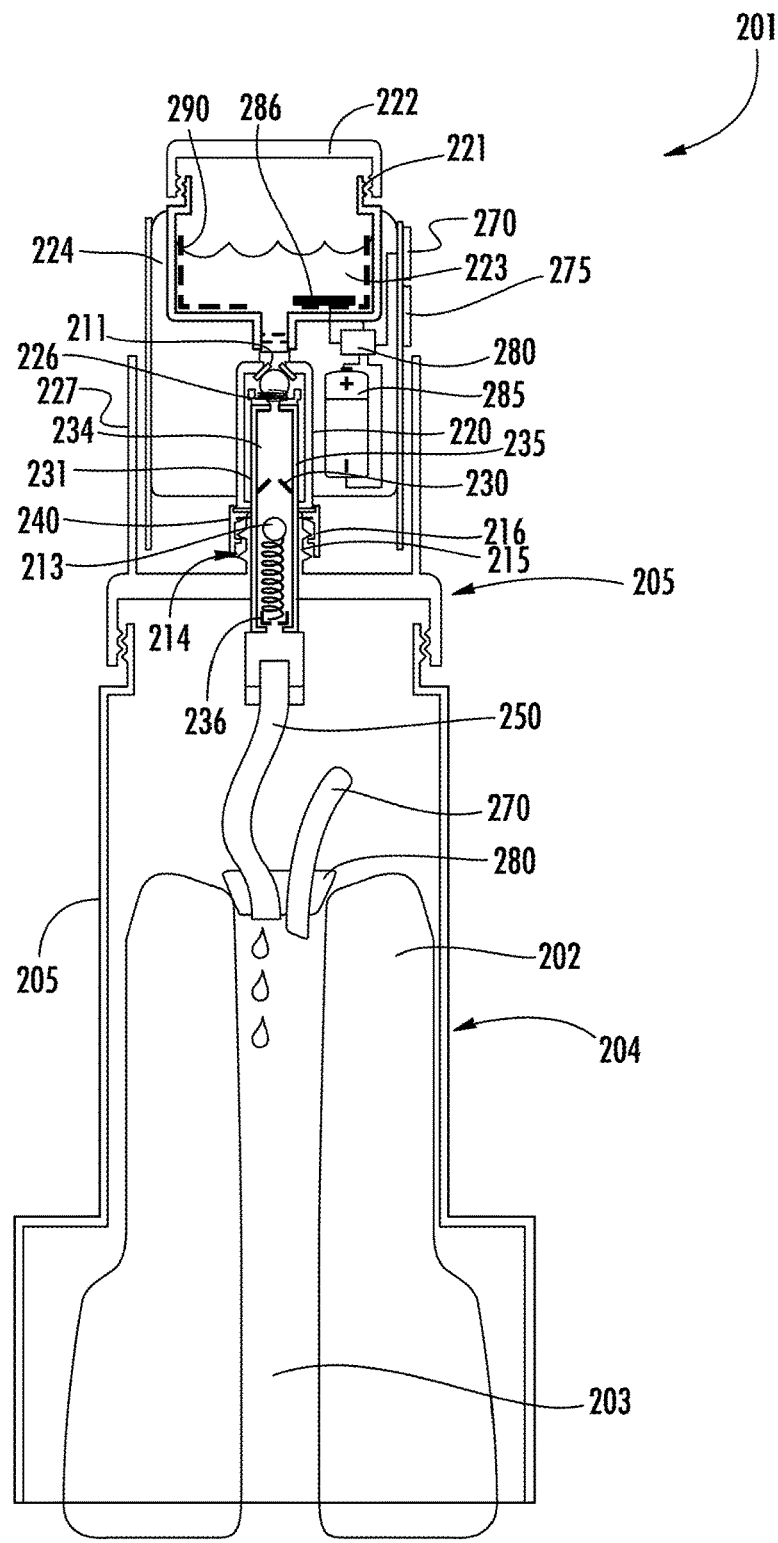

As shown in FIGS. 6A and 6B, a third embodiment of the assembly 201 includes a lock mechanism 214 with a first screw thread 216 that screws onto a second screw thread 215 if a user pushes down on a dispensing button 224 and twists the dispensing button 224. The first screw thread 216 is arranged at an end of the dispensing button 224, and the second screw thread 215 is arranged at an end of the second housing 205 adjacent to the first housing 204. The downward and twisting movement of the dispensing button 224 engages the first screw thread 216 of the second housing 205 with the second screw thread 215 of the dispensing button 224 and causing a positive lock between the dispensing button 224 and the second housing 205 to lock the dispensing button 224 in a lower position, shown in FIG. 6b. This locking arrangement prevents further inadvertent pressing of the dispensing button 224, which may lead to undesirable spilling of lubricant 223 from the containment vessel 222. The locking arrangement also presses the first ball 226 firmly into the first valve seat 211 which prevents leakage of the lubricant 223 from the containment vessel 222.

As shown in FIGS. 6A and 6B, the third embodiment of the assembly 201 includes a temperature controller 280 in the dispensing button 224. One of ordinary skill in the art will recognize from the present application that the temperature controller 280 could be arranged anywhere within the assembly 201. The temperature controller 280 regulates current generated by a battery 285 to flow through a positive thermal resistance ceramic lining 290 of the containment vessel 222. The ceramic lining 290 of the containment vessel 222 heats up and thereby heats lubricant 223 contained therein. The temperature controller 280 is configured to heat the containment vessel 222 until the lubricant 223 therein reaches a target temperature set by a user. One of ordinary skill in the art recognizes that the temperature controller 280 can be configured to detect temperature of the lubricant 223, the containment vessel 222, or any other surrounding component. The assembly 201 includes a toggle button 275 that is configured to be engaged by a user to set a target temperature for the temperature controller 280. A display 270 is arranged on an outer surface of the assembly 201 and is configured to display (1) a current temperature of the lubricant 223 or the containment vessel 222, and (2) a target temperature of the lubricant 223 or the containment vessel 222. A thermocouple 286 is arranged within the containment vessel 222 and generates data related to the current temperature of the lubricant 223 contained within vessel 222. The thermocouple 286 is in communication with the temperature controller 280, and provides data to the temperature controller 280 regarding temperature. The temperature controller 280 can then either send a signal to the ceramic lining 290 to heat up. The third embodiment of the assembly 201 allows a user to control the temperature of the lubricant dispensed into orifice 203 for greater realism and more pleasurable and comfortable use. A lubricant vessel 231 is provided with a check valve 230 and a check valve ball 213. A valve seat 236 is provided at a bottom end of the lubricant vessel 231.

Unless otherwise described above, all components that are not specifically discussed in the second and third embodiments are similar to the components of the first embodiment, such as the first housings 4, 104, and 204, and the dispensing spouts 50, 150, 250, etc.

Figure 7:
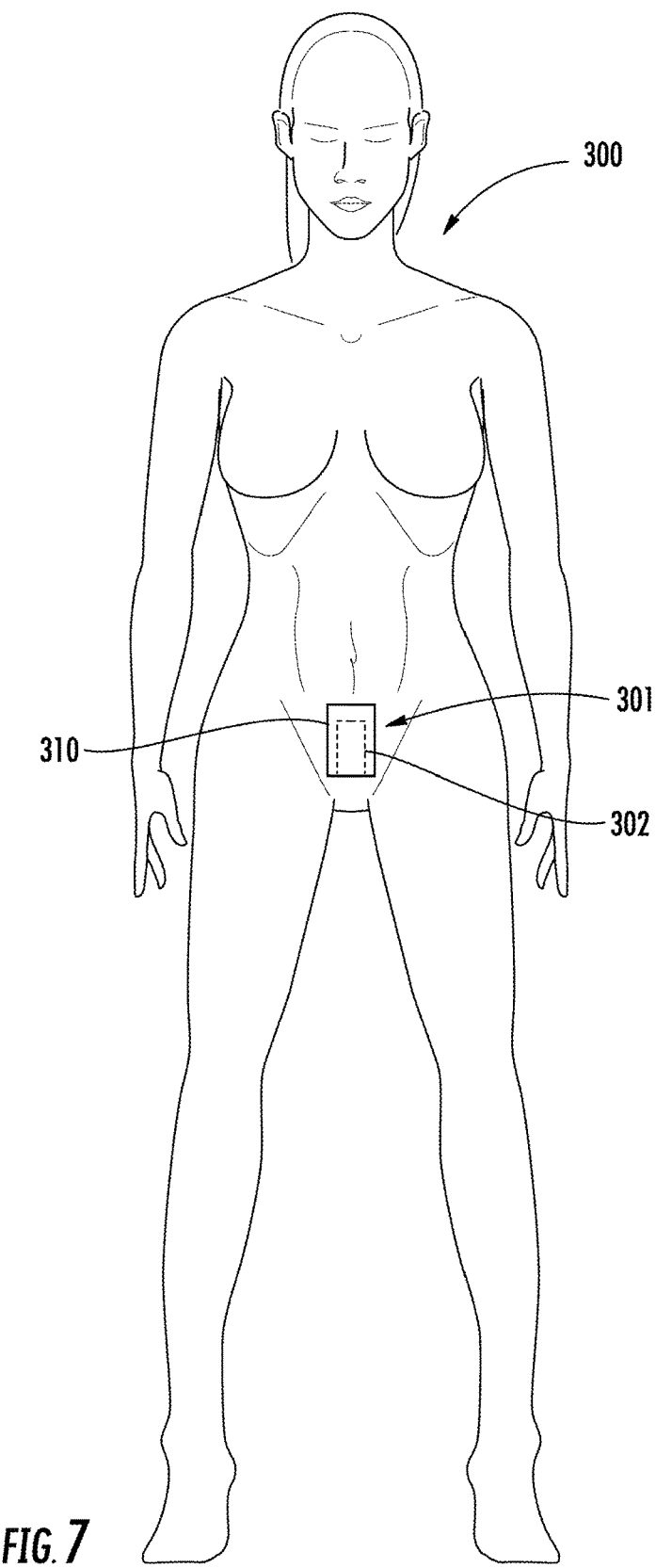
FIG. 7 illustrates a perspective view of a doll masturbation device according to an embodiment.

As shown in FIG. 7, a doll 300 is provided that includes a groin region 310 configured to receive a masturbation assembly 301. The masturbation assembly 301 of FIG. 7 can include a sleeve 302 with the same features as described above with respect to any one of the assemblies 1, 101, and/or 201. The doll 300 is of a well-known design, such as described in U.S. Pub. 2004/0122287, which is incorporated by reference as if fully set forth herein. The assemblies 1, 101, 201 can be removably attachable to the groin region 310 of the doll 300, which allows for alternatively shaped assemblies 1, 101, 201 to be inserted into the same doll 300, as well as making cleaning the assemblies 1, 101, 201 easier.

Figure 8:
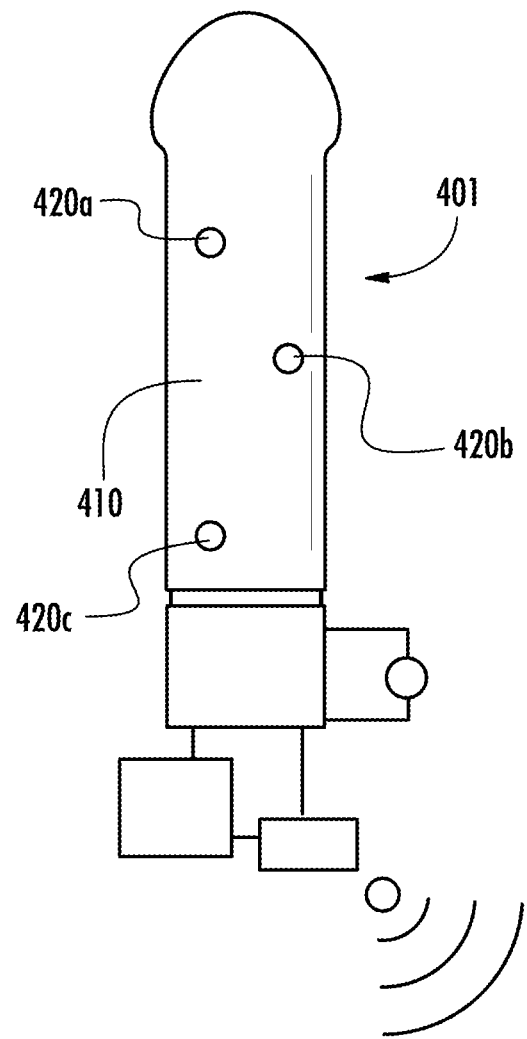
FIG. 8 illustrates a perspective view of a female masturbation device according to an embodiment.

As shown in FIG. 8, a masturbation assembly 401 is provided including an elongated member 410. The elongated member 410 is similar to the device as shown and described in U.S. Patent Pub. 2015/0366748, which is incorporated by reference as if fully set forth herein. The elongated member 410 is preferably shaped to resemble a penis. In one embodiment, the masturbation assembly 401 is configured to include the containment vessel 22 of the first embodiment of the assembly 1, such that the masturbation assembly 401 can controllably supply lubrication to the elongated member 410. The elongated member 410 can include a plurality of ports 420a, 420b, 420c axially and circumferentially spaced apart from one another as shown in FIG. 8. The plurality of ports 420a, 420b, 420c can be provided in any spatial configuration and are configured to controllably receive and distribute lubrication to the elongated member 410. The heating elements and/or the motorized elements described above can be incorporated into the masturbation assembly 401. The masturbation assembly 401 can also include a wireless transmitter for receiving impulse signals similar to element 130 in FIG. 5.

Figure 9A:
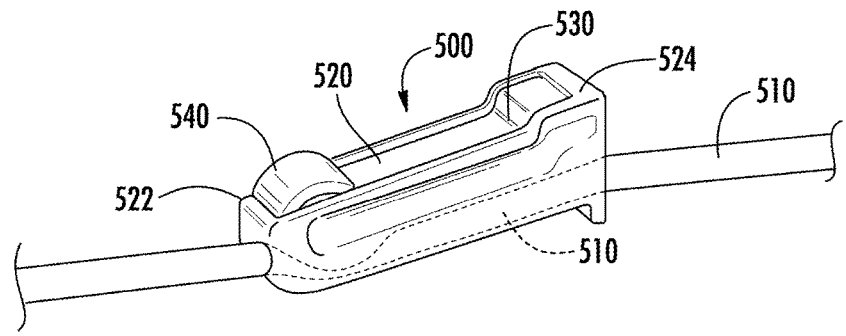
FIGS. 9A and 9B illustrate a flow regulator assembly according to an embodiment.
Figure 9B:
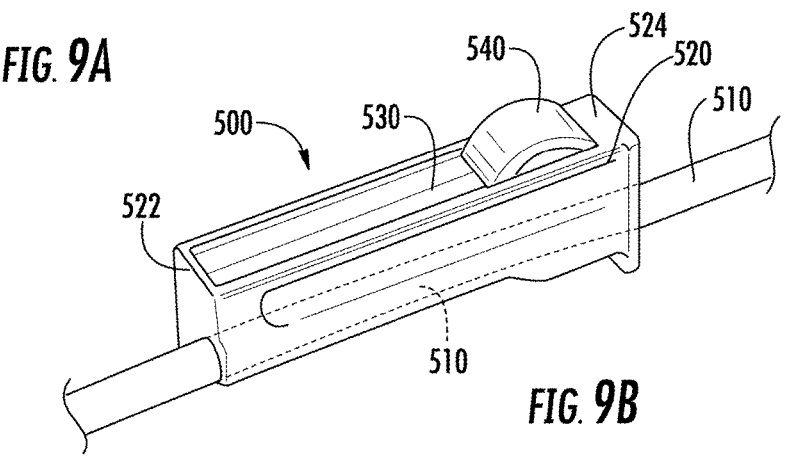

As shown in FIGS. 9A and 9B, a flow regulator 500 is provided that controls a flow of fluid or lubricant. The flow regulator 500 includes a tube 510 that passes through a regulator housing 520. The regulator housing 520 defines a channel 530 and includes a knob 540 that is slidably arranged within the channel 530. The knob 540 is guided within the channel 530 on an angle such that a first passage is defined between the knob 540 and an internal portion of the regulator housing 520 at a first end 522 of the regulator housing 520 (shown in FIG. 9A), and a second passage is defined between the knob 540 and the internal portion of the regulator housing 520 at a second, opposite end 524 of the regulator housing 520 (shown in FIG. 9B). As illustrated by dashed lines in FIG. 9A, the tube 510 is completely pinched when the knob 540 is at the first end 522 of the regulator housing 520, which results in a blockage of any fluid or lubricant from passing through the flow regulator 500. Once the knob 540 is moved away from the first end of the regulator housing 520 towards the second end 524 of the regulator housing 520, the flow of fluid or lubricant increases as the pinching of the tube 510 is relieved. The knob 540 can consist of a toothed wheel that rotates as it is pushed in either direction within the channel 530 of the regulator housing 520. The flow of fluid or lubricant can vary from a complete blockage of fluid or lubricant when the knob 540 is at the first end 522 of the regulator housing 520 to an unimpeded flow of fluid or lubricant when the knob 540 is at the second end 524 of the regulator housing 520. A partial flow can be regulated by positioning the knob 540 at any position between the first end 522 and the second end 524. Once a user sets the knob 540 in a position within the channel 530, the knob 540 is locked in a set position until the user once again engages the knob 540.

Figure 10:
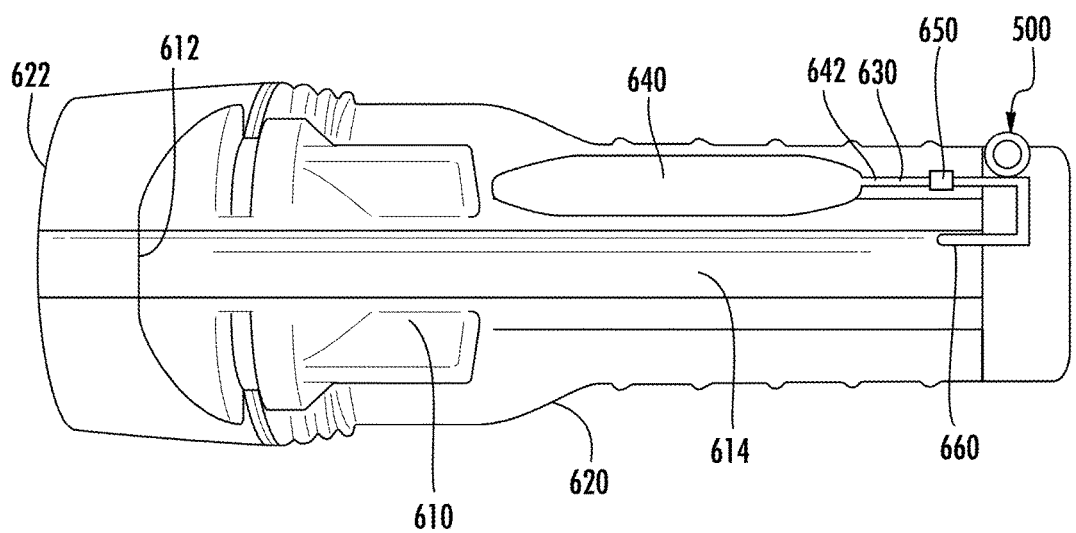
FIG. 10 illustrates a dispensing mechanism for lubrication for a sleeve according to an embodiment.

FIG. 10 illustrates a dispensing mechanism 600 including the flow regulator 500 of FIGS. 9A and 9B. The dispensing mechanism 600 controls the flow of fluid or lubrication to a sleeve 610. The dispensing mechanism 600 includes a housing 620 with the sleeve 610 arranged within the housing 620. The sleeve 610 includes a sleeve orifice 612 that is aligned with a housing orifice 622. The orifices 612, 622 are dimensioned to receive a user's sexual organ, i.e. a user's penis. The dispensing mechanism 600 includes a lubricant supply assembly 630 with a lubricant reservoir balloon 640. The lubricant reservoir balloon 640 defines a pocket for lubrication. One of ordinary skill in the art recognizes that lubrication could be resupplied to the lubricant reservoir balloon 640 via an external screw cap, or removing and refilling the lubricant reservoir balloon 640. The lubricant reservoir balloon 640 is formed from a polymeric or rubber material and contracts as lubrication exits the lubricant reservoir balloon 640. A tube 642 extends between the lubricant reservoir balloon 640 and an end 660 of the tube 642 that terminates within the sleeve 610. The tube 642 directs lubrication from the lubricant reservoir balloon 640 into the sleeve 610. A one-way check valve 650 is arranged within the tube 642 which prevents backflow of the lubricant backward to the lubricant reservoir balloon 640. As shown in FIG. 10, the flow regulator 500 is arranged on the tube 642 adjacent to the check valve 650. The lubricant reservoir balloon 640 is arranged adjacent to an internal region 614 of the sleeve 610. As shown in FIG. 10, the internal region 614 is defined longitudinally inwards from the sleeve orifice 612. As a user penetrates the dispensing mechanism 600 and the user's sex organ is inserted within the internal region 614 of the sleeve 610, the sleeve 610 is forced radially outwards in an area of the internal region 614 which compresses and squeezes the lubricant reservoir balloon 640. As the lubricant reservoir balloon 640 is compressed and squeezed due to a radially outward pressure from the sleeve 610 due to the user's sex organ, the lubricant reservoir balloon 640 forces lubricant out of the lubricant reservoir balloon 640 and into the tube 642. The flow regulator 500 then modulates the flow of this lubricant which is expelled from the lubricant reservoir balloon 640 to the terminating end 660 of the tube 642 within the sleeve 610. The dimensions of the lubricant reservoir balloon 640 can be modified to be larger or smaller, which would alter the amount of input pressure from a user's sexual organ required to deform the internal region 614 of the sleeve 610 to disperse lubricant. The dispensing mechanism 600 does not require any mechanized pump or lubricant dispensing device, and as such, this embodiment is considered a "self-lubricating" configuration due to its lack of external motors, pumps, or other devices required for pumping lubricant to the sleeve. A user can adjust the volume of lubricant that is expelled from the lubricant reservoir balloon 640 by adjusting the position of the knob 540 on the flow regulator 500.

Figure 11:
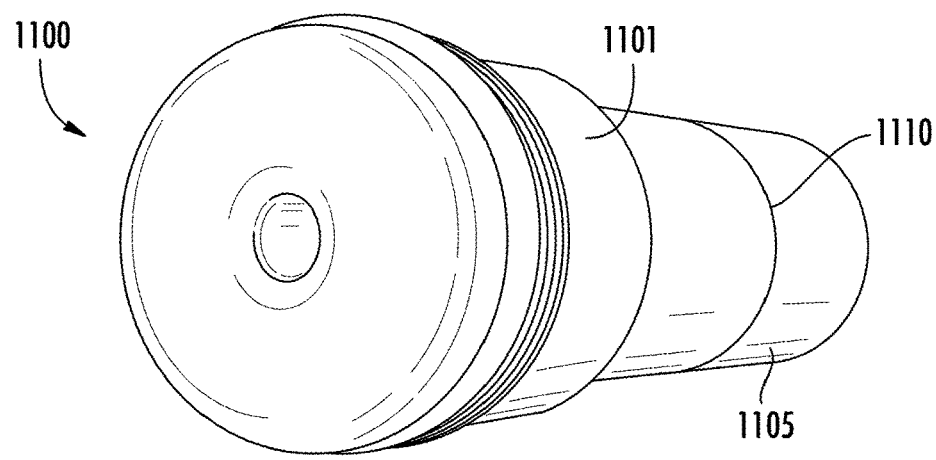
FIG. 11 illustrates a perspective view of a masturbation assembly attached to a sex toy.

FIG. 11 illustrates a perspective view of a masturbation assembly 1100 including a sex toy housing 1101 and a pump housing assembly 1105 attached to the end of the sex toy housing 1101. Existing sex toy housings 1101 include an opening on an opposite end of an orifice intended to accommodate a sex organ of a user. This opening is typically referred to as an exhaust opening. The pump housing assembly 1105 can be screwed onto a corresponding threading on the end of the sex toy housing 1101 or otherwise fastened to the end of the sex toy housing 1101. The pump housing assembly 1105 can provide lubricant to an internal area of a sleeve of the sex toy housing 1101 via any one of the pumps described above. For example, the pump housing assembly 1105 can include the lubricant reservoir 23, check valve 33, and lubricant dispensing elements discussed above. A dispensing spout (similar to the one described above as dispensing spout 50 in FIGS. 2A-2C) can then provide a controlled release of lubricant from inside the pump housing assembly 1105 to the inside of the sex toy housing 1101. The sex toy housing 1101 can include any known existing sex toy, such as a Fleshlight® sex toy. The pump housing assembly 1105 includes an attaching end 1110 that is configured to fasten to an existing exhaust end of the sex toy housing 1101. The attaching end 1110 is dimensioned to fixedly engage with an existing sex toy. The attaching end 1110 can include a mating thread for the exhaust end of the sex toy housing 1101 or a deformable portion that can be plugged into the exhaust end of the sex toy housing 1101 such that the pump housing assembly 1105 is mated with the sex toy housing 1101. The pump housing 1105 can include any of the features described above, such as a wireless connection, Bluetooth® connection, heating element, mechanized pump element, display element, or any of the elements discussed above in FIGS. 1-10.

Figure 12A:
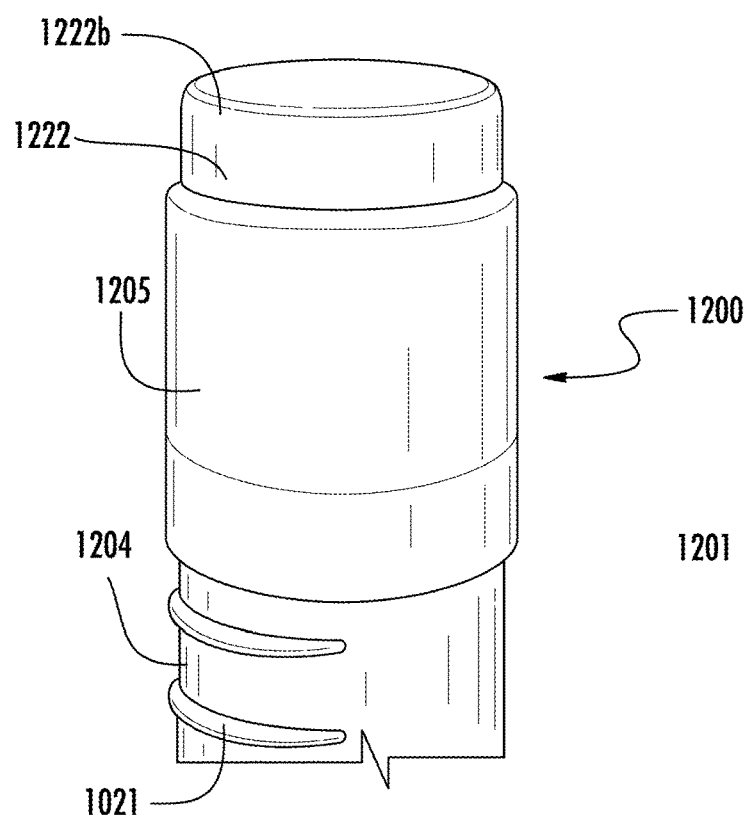
FIG. 12A illustrates a perspective view of a masturbation assembly attached to a sex toy.
Figure 12B:
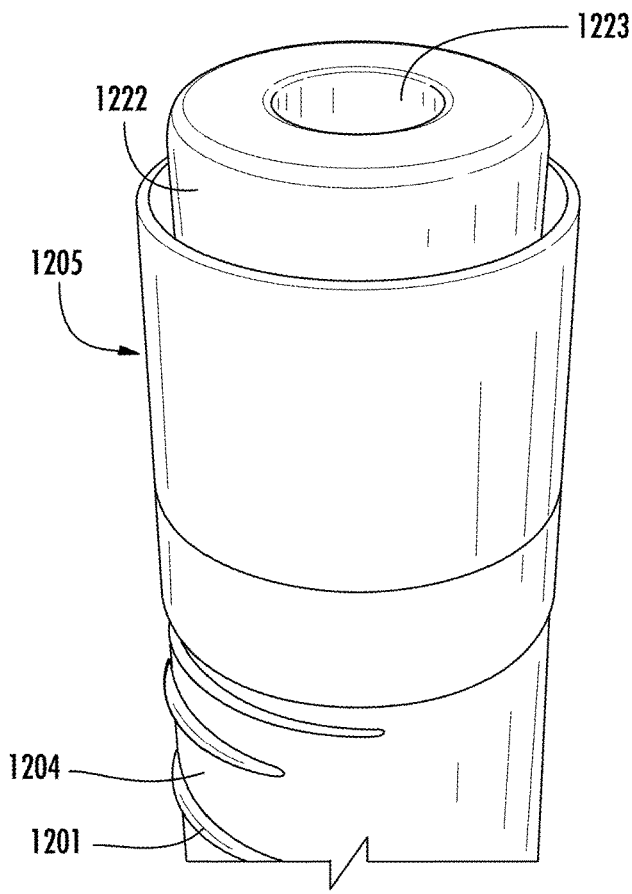
FIG. 12B illustrates a top perspective view of the masturbation assembly of FIG. 12A without a cap.
Figure 12C:
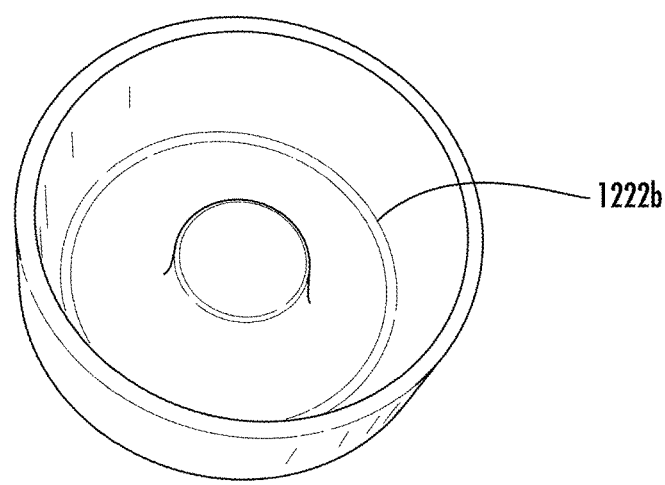
FIG. 12C illustrates the cap of the masturbation assembly shown in FIG. 12A.
Figure 12D:
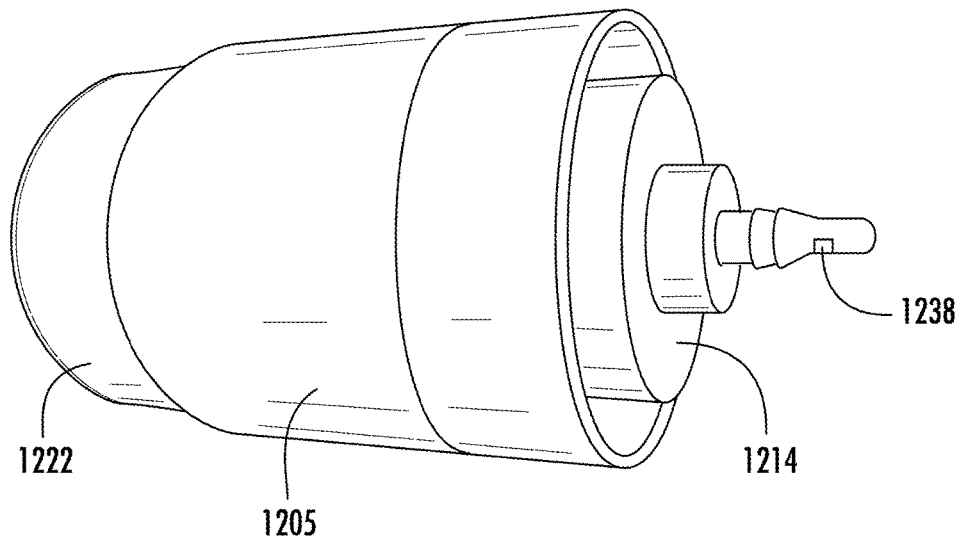
FIG. 12D illustrates the masturbation assembly of 12A detached from a sex toy.
Figure 12E:
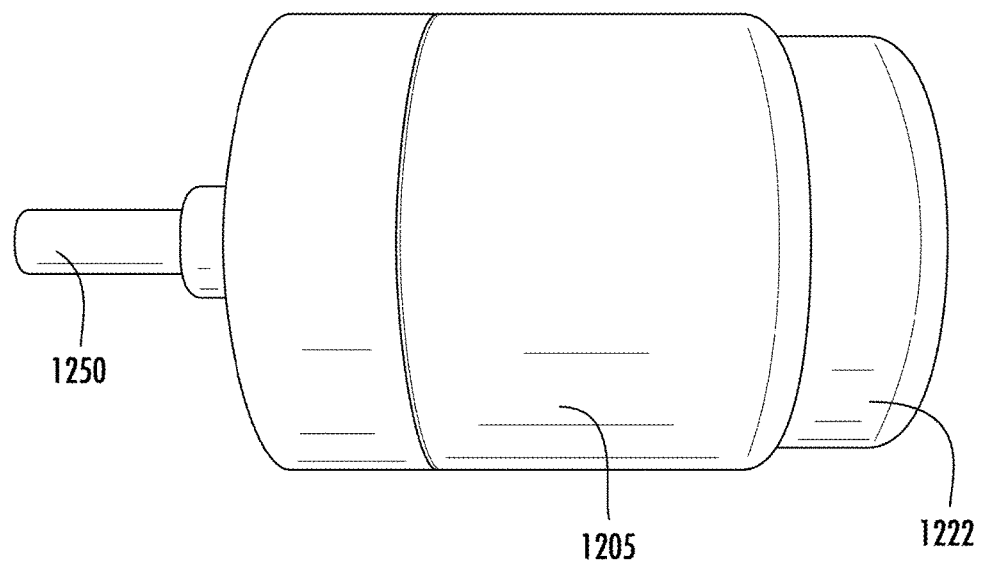
FIG. 12E illustrates the masturbation assembly of FIG. 12A detached from a sex toy.

FIGS. 12A-12E illustrate a masturbation assembly 1200 attached to an existing sex toy 1201. As shown in FIG. 12A, the masturbation assembly 1200 is dimensioned to be attached to an end 1204 of the sex toy 1201. The masturbation assembly 1200 includes a flexible sleeve that is attachable to the end 1204 of the sex toy 1201. The assembly 1200 includes a pump housing assembly 1205, similar to the second housing 5 described above. The assembly 1200 includes a containment vessel 1222 and a corresponding cap 1222b to hold the lubricant within the containment vessel 1222. FIG. 12B illustrates the assembly 1200 without the cap 1222b, and FIG. 12C shows an underside of the cap 1222b. FIG. 12D illustrates the masturbation assembly 1200 detached from the sex toy 1201. In this view, a stem 1238 with an opening for lubricant is shown. This stem 1238 extends into an opening on the sex toy 1201 in the assembled state shown in FIG. 12A. A locking member 1214 is shown in this view which attaches the masturbation assembly 1200 to the sex toy 1201 in the assembled state. FIG. 12E illustrates the masturbation assembly 1200 with a dispensing spout 1250 surrounding the stem 1238. The dispensing spout 1250 extends into the sex toy 1201 in an assembled state and directs lubricant to the internal area of a sleeve of the sex toy 1201.

In another embodiment, the lubricant reservoir is contained in a housing, similar to the first housing 4, and the housing is a disposable cartridge. The disposable cartridge can be attached to any existing sex toy. The disposable cartridge can be squeezed or otherwise activated to dispense lubricant downwards to an orifice of a sex toy. The disposable cartridge can include a thread, snap-on, or other fastening means to attach the disposable cartridge to the sex toy.

One of ordinary skill in the art would recognize that any of the components from any one of the Figures could be incorporated into any other one of the Figures with slight modifications.

What is claimed is:

1. A lubricant supply assembly for removable engagement with a terminal engagement end of a sex toy housing,
   the sex toy housing including an elastomeric sleeve defining an internal chamber including an opening opposite the terminal engagement end,
   the lubricant supply assembly comprising:
   a lubricant housing including a lubricant reservoir and a lubricant delivery assembly, the lubricant housing adapted for removable attachment to the terminal engagement end of the sex toy housing such that at least a portion of the lubricant reservoir is positioned outside the internal chamber of the sex toy housing; and
   an actuator in communication with the lubricant housing, the actuator configured to selectively block or permit a flow of lubricant from the lubricant reservoir to the lubricant delivery assembly and to an interior of the elastomeric sleeve.

2. The lubricant supply assembly of claim 1, further comprising a valve positioned between the lubricant reservoir and the lubricant delivery assembly, the valve controlling the flow of lubricant between the lubricant reservoir and the lubricant delivery assembly.

3. The lubricant supply assembly of claim 2, wherein the actuator includes a CPU unit that controls the valve.

4. The lubricant supply assembly of claim 1, wherein the lubricant delivery assembly includes a sensor configured to detect an impulse, and the impulse is used by the lubricant supply assembly to adjust the volume, temperature, frequency or other variable of the lubricant.

5. The lubricant supply assembly of claim 1, further comprising a heater unit provided to heat the lubricant in the lubricant reservoir based on signals received from a CPU unit.

6. A lubricant supply assembly for removable engagement with an engagement end of a sex toy housing,
   the sex toy housing including an elastomeric sleeve defining an opening opposite the engagement end,
   the lubricant supply assembly comprising:
   a lubricant housing including a lubricant reservoir and a lubricant delivery assembly, the lubricant housing being adapted for removable attachment to the engagement end of the sex toy housing;

an actuator in communication with the lubricant housing, the actuator configured to selectively block or permit a flow of lubricant from the lubricant reservoir to the lubricant delivery assembly and to an interior of the elastomeric sleeve, and a dispensing spout that receives lubricant from the lubricant reservoir and directs lubricant to an outlet positioned in a medial interior region of the elastomeric sleeve.

7. The lubricant supply assembly of claim 6, further comprising a plurality of dispensing spouts extending between the lubricant housing and the sex toy housing, each of the plurality of dispensing spouts terminates spaced apart from one another along the sex toy housing in an axial and circumferential direction with respect to the sex toy housing.

8. The lubricant supply assembly of claim 1, further comprising a temperature controller, a battery, and a ceramic lining within the lubricant housing, wherein the ceramic lining heats lubricant within the lubricant reservoir.

9. The lubricant supply assembly of claim 1, further comprising a motor for driving the actuator.

10. The lubricant supply assembly of claim 9, wherein the actuator is a pump or displacement screw.

11. The lubricant supply assembly of claim 1, further comprising an adjustable dial for adjusting a speed of the actuator.

12. The lubricant supply assembly of claim 1, further composing a heater and a processor that sets a target temperature of the lubricant within the lubricant reservoir.

13. The lubricant supply assembly of claim 12, wherein the lubricant housing includes a display configured to display the target temperature of the lubricant within the lubricant reservoir and a current temperature of the lubricant within the lubricant reservoir.

14. The lubricant supply assembly of claim 1, further comprising a processor for receiving an input signal, wherein the input signal from the processor is used to selectively control the speed of the actuator.

15. The lubricant supply assembly of claim 14, further comprising a wireless transmitter/receiver unit that receives the input signal for the processor.

16. The lubricant supply assembly of claim 1, wherein the lubricant housing includes a threading that mates with a threading on the terminal engagement end of the sex toy housing.

17. A lubricant supply assembly for removable engagement with a terminal engagement end of a sex toy housing, the sex toy housing including an outer shell and an elastomeric sleeve arranged within the outer shell and defining an opening opposite the terminal engagement end, the lubricant supply assembly comprising:

a lubricant housing including a lubricant reservoir and a lubricant delivery assembly, the lubricant reservoir at least partially arranged in a radial space defined between the outer shell and the elastomeric sleeve; and an actuator in communication with the lubricant housing, the actuator configured to selectively block or permit a flow of lubricant from the lubricant reservoir to the lubricant delivery assembly and to an interior of the elastomeric sleeve.

18. A lubricant supply assembly for removable engagement with a terminal engagement end of a sex toy housing, the sex toy housing including an elastomeric sleeve defining an internal chamber including an opening opposite the terminal engagement end, the lubricant supply assembly comprising:

a lubricant housing including a lubricant reservoir and a lubricant delivery assembly, the lubricant housing adapted for removable attachment to the terminal engagement end of the sex toy housing such that at least a portion of the lubricant supply assembly is positioned outside the internal chamber of the sex toy housing; and an actuator in communication with the lubricant housing, the actuator configured to selectively block or permit a flow of lubricant from the lubricant reservoir to the lubricant delivery assembly and to an interior of the elastomeric sleeve.

* * * * *